United States Patent
Stigall et al.

(10) Patent No.: US 10,973,491 B2
(45) Date of Patent: Apr. 13, 2021

(54) INTERCONNECTS FOR INTRAVASCULAR ULTRASOUND (IVUS) DEVICES

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 68 days.

(21) Appl. No.: 15/735,882

(22) PCT Filed: May 19, 2016

(86) PCT No.: PCT/IB2016/052933
§ 371 (c)(1),
(2) Date: Dec. 12, 2017

(87) PCT Pub. No.: WO2016/198975
PCT Pub. Date: Dec. 15, 2016

(65) Prior Publication Data
US 2020/0037985 A1    Feb. 6, 2020

Related U.S. Application Data

(60) Provisional application No. 62/175,087, filed on Jun. 12, 2015.

(51) Int. Cl.
*A61B 8/00* (2006.01)
*A61B 8/12* (2006.01)

(52) U.S. Cl.
CPC ............... *A61B 8/12* (2013.01); *A61B 8/445* (2013.01); *A61B 8/4488* (2013.01);
(Continued)

(58) Field of Classification Search
CPC ....... A61B 8/12; A61B 8/4494; A61B 8/4488; A61B 8/445; A61B 2562/227; A61B 2562/12; A61B 2562/028
See application file for complete search history.

(56) References Cited

U.S. PATENT DOCUMENTS

| 5,243,988 | A |   | 9/1993 | Sieben et al. |
| 5,546,948 | A | * | 8/1996 | Hamm ................. A61B 5/6848 600/463 |

(Continued)

FOREIGN PATENT DOCUMENTS

| GB | 2315020 A | 1/1998 |
| JP | 7320810 A | 12/1995 |

(Continued)

*Primary Examiner* — Joel Lamprecht

(57) ABSTRACT

Intravascular ultrasound (IVUS) imaging devices, systems, and methods are provided. Embodiments of the present disclosure provide intravascular ultrasound (IVUS) devices with robust, four-wire electrical interconnects. In some embodiments, an intravascular ultrasound (IVUS) device is provided. The IVUS device comprises: a catheter body; an ultrasound assembly coupled to a distal portion of the catheter body; and four conductors extending along a length of the catheter body, wherein a distal section of each of the four conductors has a flattened profile and wherein the flattened distal section of each of the four conductors is electrically coupled to a respective electrical contact of the ultrasound assembly. The ultrasound assembly can be a phased-array ultrasound assembly or a rotational ultrasound assembly.

17 Claims, 18 Drawing Sheets

(52) U.S. Cl.
CPC ...... *A61B 8/4494* (2013.01); *A61B 2562/028* (2013.01); *A61B 2562/12* (2013.01); *A61B 2562/227* (2013.01)

(56) References Cited

U.S. PATENT DOCUMENTS

| | | |
|---|---|---|
| 6,641,540 B2 | 11/2003 | Fleischman et al. |
| 7,846,101 B2 | 12/2010 | Eberle et al. |
| 8,104,479 B2 | 1/2012 | Glynn et al. |
| 8,864,674 B2 * | 10/2014 | Corl ................ A61B 8/4494 600/462 |
| 2010/0023473 A1 | 1/2010 | Neumann |
| 2013/0303919 A1 | 11/2013 | Corl |
| 2014/0187960 A1 | 7/2014 | Corl |
| 2014/0371744 A1 * | 12/2014 | Dekker ............ A61B 1/0008 606/41 |

FOREIGN PATENT DOCUMENTS

| | | | |
|---|---|---|---|
| JP | 2003257749 | * | 3/2002 |
| JP | 2003257749 A | | 9/2003 |
| JP | 2004047144 A | | 2/2004 |
| JP | 2004063253 A | | 2/2004 |
| JP | 2004281151 A | | 10/2004 |
| JP | 2010118380 A | | 5/2010 |

\* cited by examiner

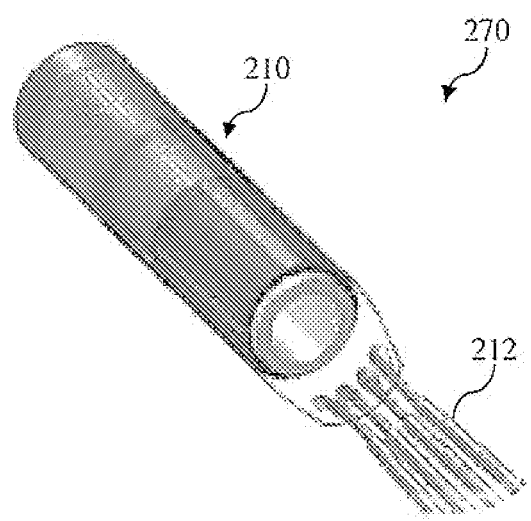
Fig. 8
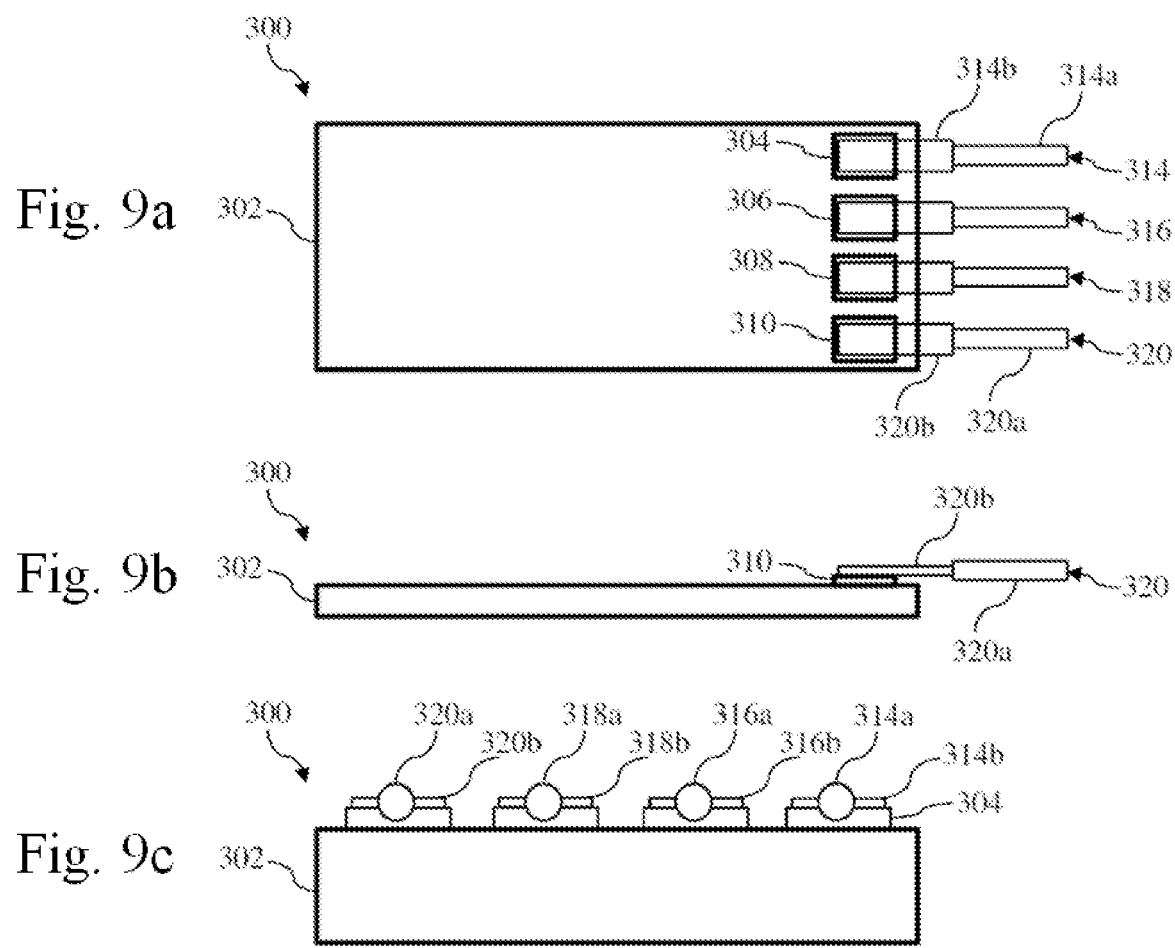
Fig. 9a
Fig. 9b
Fig. 9c

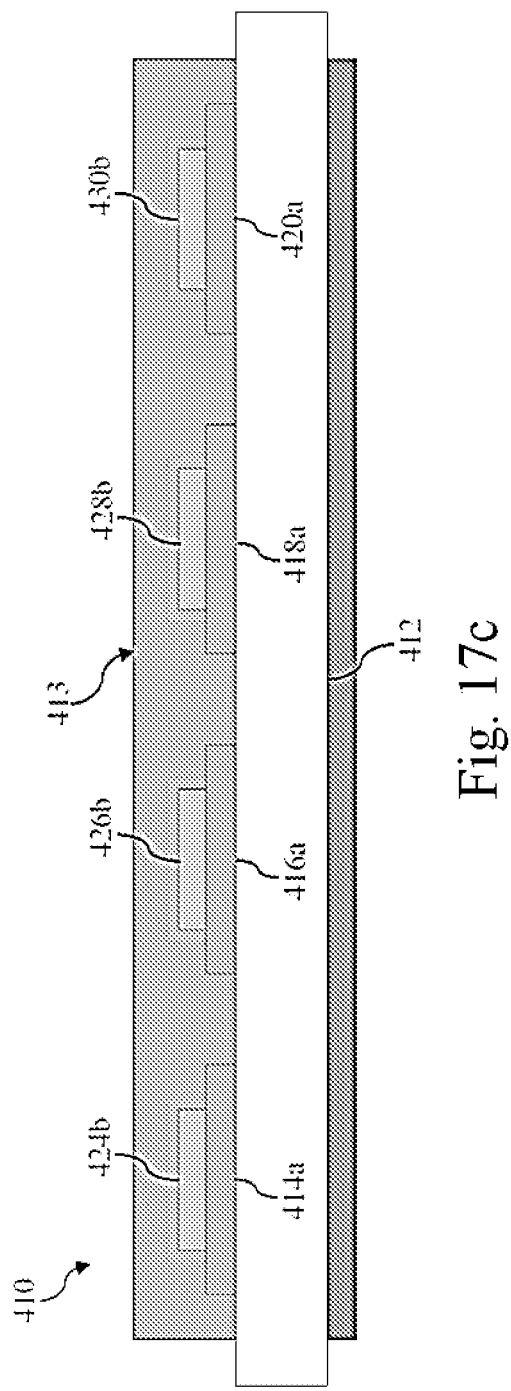

INTERCONNECTS FOR INTRAVASCULAR ULTRASOUND (IVUS) DEVICES

CROSS-REFERENCE TO PRIOR APPLICATIONS

This application is the U.S. National Phase application under 35 U.S.C. § 371 of International Application No. PCT/IB2016/052933, filed on May 19, 2016, which claims the benefit of U.S. Provisional Patent Application No. 62/175,087, filed on Jun. 12, 2015. These applications are hereby incorporated by reference herein.

TECHNICAL FIELD OF THE INVENTION

The present disclosure relates generally to intravascular ultrasound (IVUS) imaging inside a living body.

BACKGROUND OF THE INVENTION

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. To perform an IVUS imaging study, an IVUS catheter that incorporates one or more ultrasound transducers is passed into the vessel and guided to the area to be imaged. The transducers emit and receive ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by a transducer and passed along to an IVUS imaging system, which is connected to the IVUS catheter by way of a patient interface module (PIM). The imaging system processes the received ultrasound signals to produce a cross-sectional image of the vessel where the device is placed.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS catheters carry an ultrasound scanner assembly that includes an array of ultrasound transducers distributed around the circumference of the device connected to a set of transducer control circuits. The transducer control circuits select individual transducers for transmitting an ultrasound pulse and for receiving the echo signal. By stepping through a sequence of transmitter-receiver pairs, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable and a standard detachable electrical connector.

One factor in IVUS catheter performance is catheter agility. Rotational catheters tend to smoothly advance around corners due to the flexible rotating drive shaft contained within the sheath. However, rotational catheters often require a long rapid exchange tip to engage the guidewire, and the long tip may limit the advance of the imaging core containing the transducer. For example, this may prevent the catheter from being advanced to very distal locations within the coronary arteries. On the other hand, solid-state IVUS catheters may have a shorter tip as the guidewire can pass through the interior lumen of the scanner. However, some solid-state designs have rigid segments that limit the ability to advance the catheter around sharp bends in the vasculature. Solid-state IVUS catheters also tend to be larger in diameter than rotational catheters to accommodate the transducer array and the associated electronics.

Another factor limiting catheter performance is the number of electrical conductors or wires extending along the length of the device to facilitate the communication of signals to and from the ultrasound transducer(s). For example, in some current commercial products seven wires extend along the length of the catheter between a proximal connector and the ultrasound assembly at the distal portion of the catheter. Due to the relatively large number of conductors required and the limited space within the catheter, the connections to the ultrasound assembly typically must be very small and, therefore, can be prone to breakage/failure during the manufacturing process, transportation, and/or use.

While existing IVUS imaging systems have proved useful, there remains a need for improvements in the design of the electrical interconnects utilized in IVUS catheters to facilitate use of a fewer number of electrical leads and increase the durability of the devices. Accordingly, the need exists for improvements to the interconnect designs utilized in IVUS catheter and the associated manufacturing techniques.

SUMMARY OF THE INVENTION

Embodiments of the present disclosure provide intravascular ultrasound (IVUS) devices with robust, four-wire electrical interconnects.

In some embodiments, an intravascular ultrasound (IVUS) device is provided. The IVUS device comprises: a catheter body; an ultrasound assembly coupled to a distal portion of the catheter body; and four conductors extending along a length of the catheter body, wherein a distal section of each of the four conductors has a flattened profile and wherein the flattened distal section of each of the four conductors is electrically coupled to a respective electrical contact of the ultrasound assembly. The ultrasound assembly can be a phased-array ultrasound assembly or a rotational ultrasound assembly.

The electrical contacts of the ultrasound assembly can be bond pads. In some instances, the distal section of each of the four conductors is electrically and mechanically coupled to the respective bond pad of the ultrasound assembly by at least one of a solder, a resistance weld, or a conductive adhesive. The electrical contacts of the ultrasound assembly can include an upper portion and a lower portion such that the distal section of each of the four conductors is positioned between the upper and lower portions of the respective electrical contact. The distal section of each of the four conductors can be electrically and mechanically coupled to the respective electrical contact of the ultrasound assembly by at least one of a solder, a resistance weld, or a conductive adhesive and/or the distal section of each of the four conductors can be press fit between the upper and lower portions of the respective electrical contact. The electrical contacts of the ultrasound assembly can include an opening such that the distal section of each of the four conductors is positioned within the opening of the respective electrical contact. In some instances, each of the electrical contacts is crimped to the distal section of each of the four conductors to electrically and mechanically couple the distal section of each of the four conductors to the respective electrical contact of the ultrasound assembly. The crimping of the electrical contact to the distal section of the conductor can define the flattened profile of the distal section of the conductor in some instances. The distal section of each of the four conductors can be mechanically coupled to the respective electrical contact of the ultrasound assembly by at least one of a locking pin or a locking screw.

In some embodiments, an intravascular ultrasound (IVUS) system is provided that includes an IVUS imaging device comprising: a catheter body; an ultrasound assembly coupled to a distal portion of the catheter body; a proximal connector coupled to a proximal portion of the catheter body; and four conductors extending along a length of the catheter body, wherein a distal section of each of the four conductors has a flattened profile and wherein the flattened distal section of each of the four conductors is electrically coupled to a respective electrical contact of the ultrasound assembly, and wherein a proximal section of each of the four conductors is coupled to the proximal connector; an interface module configured to connect with the proximal connector of the imaging device; and an intravascular ultrasound (IVUS) processing component in communication with the interface module.

In some embodiments, a method of forming an intravascular imaging device is provided that includes providing an ultrasound assembly; providing four conductors; electrically coupling a distal section of each of the four conductors to a respective electrical contact of the ultrasound assembly, wherein the distal section of each of the four conductors has a flattened profile; and coupling the ultrasound assembly to a distal portion of a catheter body and extending the four conductors along a length of the catheter body. The electrical contacts of the ultrasound assembly can be bond pads and the step of electrically coupling the distal section of each of the four conductors to the respective bond pad of the ultrasound assembly includes at least one of soldering, resistance welding, or applying a conductive adhesive.

In some instances, each of the electrical contacts of the ultrasound assembly includes an upper portion and a lower portion and the method further includes positioning the distal section of each of the four conductors between the upper and lower portions of the respective electrical contact. Electrically coupling the distal section of each of the four conductors to the respective electrical contact of the ultrasound assembly can include at least one of soldering, resistance welding, or applying a conductive adhesive. Electrically coupling the distal section of each of the four conductors to the respective electrical contact of the ultrasound assembly can also include press fitting the distal section of each of the four conductors between the upper and lower portions of the respective electrical contact.

In some instances, each of the electrical contacts of the ultrasound assembly includes an opening and the method further includes positioning the distal section of each of the four conductors within the opening of the respective electrical contact. Electrically coupling the distal section of each of the four conductors to the respective electrical contact of the ultrasound assembly can include crimping each of the electrical contacts to the distal section of each of the respective four conductors. In this regard, crimping the electrical contact to the distal section of the conductor can define the flattened profile of the distal section of the conductor. The method can further include mechanically coupling the distal section of each of the four conductors to the respective electrical contact of the ultrasound assembly by at least one of a locking pin or a locking screw.

In some embodiments, an intravascular ultrasound (IVUS) device is provided that includes a catheter body; an ultrasound assembly coupled to a distal portion of the catheter body, the ultrasound assembly including a first four-contact electrical connector; and four conductors extending along a length of the catheter body, wherein the four conductors are coupled to a second four-contact electrical connector for electrically and mechanically mating to the first four-contact electrical connector. The first four-contact electrical connector can be a female connector and the second four-contact electrical connector can be a male connector. On the other hand, the first four-contact electrical connector can be a male connector and the second four-contact electrical connector can be a female connector.

In some embodiments, a method of forming an intravascular imaging device is provided that includes providing an ultrasound assembly with a first four-contact electrical connector; providing four conductors; electrically coupling the four conductors to a second four-contact electrical connector; coupling the first and second four-contact electrical connectors together; and coupling the ultrasound assembly to a distal portion of a catheter body and extending the four conductors along a length of the catheter body.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 8 is a perspective view of an assembly with a four-wire interconnection according to the present disclosure.

FIGS. 9a-9c illustrate an assembly with a four-wire interconnection according to the present disclosure. FIG. 9a is a top view of the assembly; FIG. 9b is a side view of the assembly; and FIG. 9c is a proximal end view of the assembly.

FIGS. 10a-11c illustrate an assembly with a four-wire interconnection according to the present disclosure. FIG. 10a is a top view of the assembly without wires; FIG. 11c is a proximal end view of the assembly with wires.

FIG. 12a is a top view of the assembly; FIG. 12b is a side view of the assembly; and FIG. 12c is a proximal end view of the assembly.

FIGS. 13a-15c illustrate an assembly with a four-wire interconnection according to the present disclosure. FIG. 13a is a top view of the assembly without wires; FIG. 15c is a proximal end view of the assembly with wires crimped to the assembly.

FIG. 16a is a top view of the assembly; FIG. 16b is a side view of the assembly; and FIG. 16c is a distal end view of the assembly.

FIGS. 17a-17c illustrate an assembly with a four-wire interconnection according to the present disclosure. FIG. 17a is a top view of the assembly; FIG. 17b is a side view of the assembly; and FIG. 17c is a distal end view of the assembly.

DETAILED DESCRIPTION OF THE EMBODIMENTS

Figure 1:
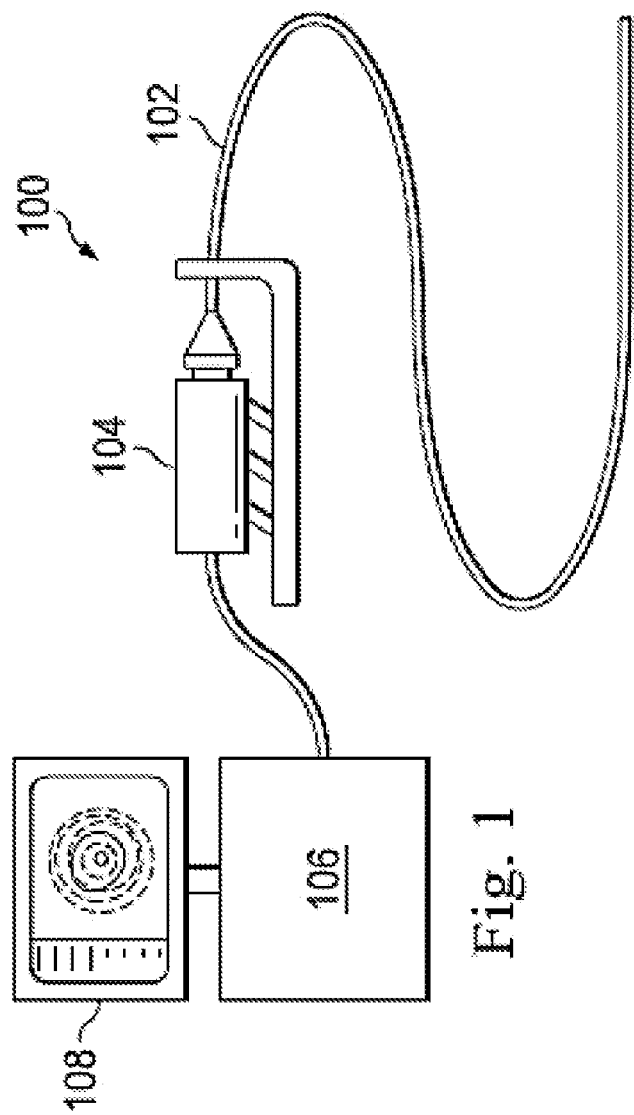
FIG. 1 is a diagrammatic schematic view of an imaging system according to the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring to FIG. 1, shown therein is an IVUS imaging system 100 according to an embodiment of the present disclosure. In particular, the IVUS imaging system 100 illustrates a rotational IVUS imaging system. In some embodiments of the present disclosure, the IVUS imaging system 100 is a PMUT rotational IVUS imaging system. However, in other embodiments the rotational IVUS imaging system 100 can utilize PZT, CMUT, and/or other types of ultrasound transducers. The main components of the PMUT rotational IVUS imaging system 100 are the PMUT rotational IVUS catheter 102, a PMUT catheter compatible patient interface module (PIM) 104, an IVUS console or processing system 106, and a monitor 108 to display the IVUS images generated by the IVUS console 106. Some of the aspects of the present disclosure that distinguish this PMUT IVUS imaging system 100 from a traditional rotational IVUS imaging system include the PMUT catheter 102 and the PMUT-compatible PIM 104 that implements the appropriate interface specifications to support the PMUT catheter 102. As discussed in greater detail below, the PMUT rotational IVUS catheter 102 includes a PMUT ultrasound transducer along with its associated circuitry mounted near a distal tip of the catheter, a four conductor electrical cable, and the appropriate electrical connector to support the rotational interface. The PMUT-compatible PIM 104 generates the required sequence of transmit trigger signals and control waveforms to regulate the operation of the circuit and processes the amplified echo signals received over that same conductor pair. The PMUT-compatible PIM 104 also supplies the high- and low-voltage DC power supplies to support operation of the PMUT rotational IVUS catheter 102. An important feature of the PMUT-compatible PIM 104 is that it must deliver DC supply voltages to the PMUT circuitry of the catheter 102 across a rotational interface. This requirement largely precludes the option of a rotary transformer, commonly used for traditional rotational IVUS systems, since a transformer can only convey AC signals from the primary to the secondary side. Practical options for delivering DC power across a rotating interface include the use of slip-rings and/or the implementation of the active spinner technology described in U.S. Patent Application Publication No. 2010/0234736, which is hereby incorporated by reference in its entirety.

Figure 2:
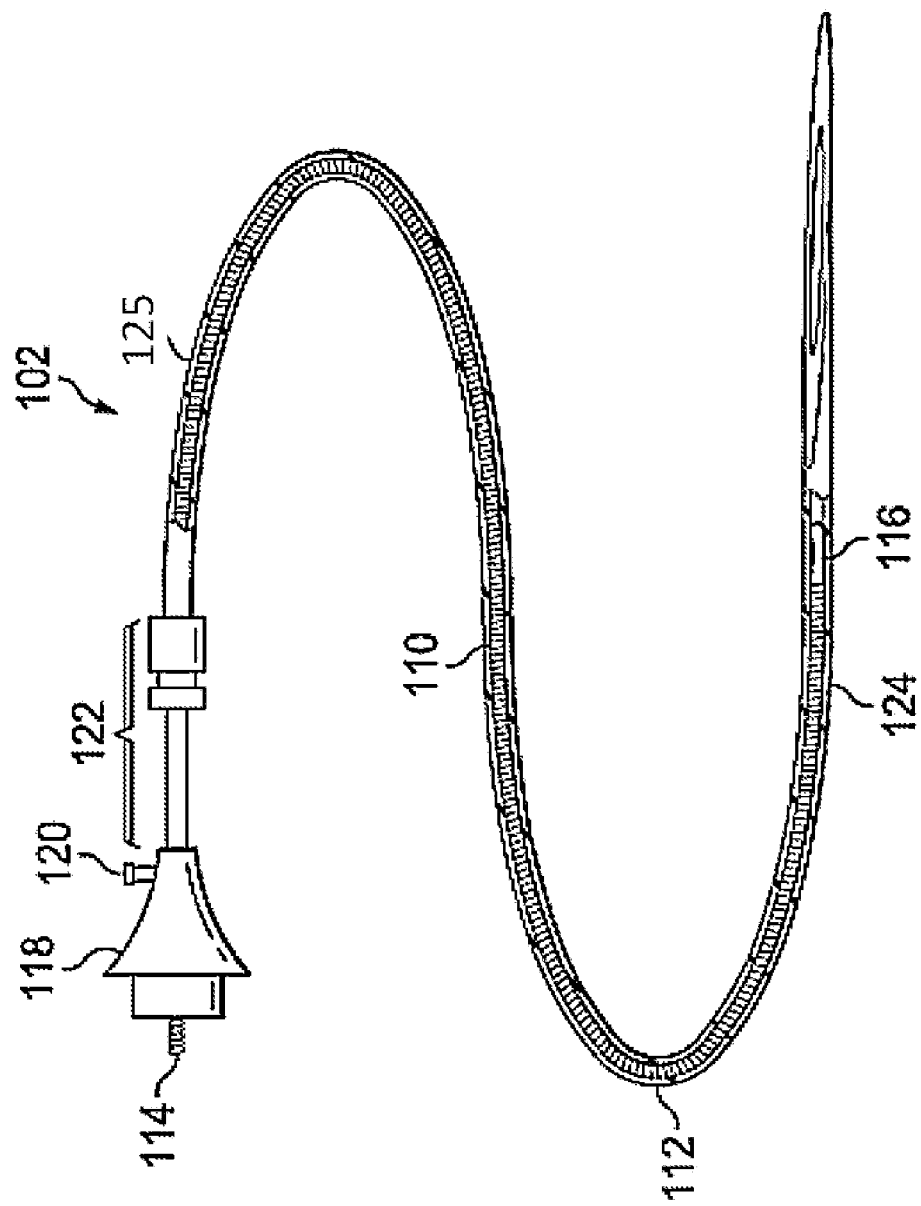
FIG. 2 is a diagrammatic, partial cutaway perspective view of an imaging device according to the present disclosure.

Referring now to FIG. 2, shown therein is a diagrammatic, partial cutaway perspective view of the PMUT catheter 102 according to an embodiment of the present disclosure. In that regard, FIG. 2 shows additional detail regarding the construction of the PMUT rotational IVUS catheter 102. In many respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, the PMUT rotational IVUS catheter 102 includes an imaging core 110 and an outer catheter/sheath assembly 112. The imaging core 110 includes a flexible drive shaft that is terminated at the proximal end by a rotational interface 114 providing electrical and mechanical coupling to the PIM 104 of FIG. 1. The distal end of the flexible drive shaft of the imaging core 110 is coupled to a transducer housing 116 containing the PMUT and associated circuitry, which are described in greater detail below. The catheter/sheath assembly 112 includes a hub 118 that supports the rotational interface and provides a bearing surface and a fluid seal between the rotating and non-rotating elements of the catheter assembly. The hub 118 includes a luer lock flush port 120 through which saline is injected to flush out the air and fill the inner lumen of the sheath with an ultrasound-compatible fluid at the time of use of the catheter. The saline or other similar flush is typically required since air does not readily conduct ultrasound. Saline also provides a biocompatible lubricant for the rotating driveshaft. The hub 118 is coupled to a telescope 122 that includes nested tubular elements and a sliding fluid seal that permit the catheter/sheath assembly 112 to be lengthened or shortened to facilitate axial movement of the transducer housing within an acoustically transparent window 124 of the distal portion of the catheter 102. In some embodiments, the window 124 is composed of thin-walled plastic tubing fabricated from material(s) that readily conduct ultrasound waves between the transducer and the vessel tissue with minimal attenuation, reflection, or refraction. A proximal shaft 125 of the catheter/sheath assembly 112 bridges the segment between the telescope 122 and the window 124, and is composed of a material or composite that provides a lubricious internal lumen and optimum stiffness, but without the need to conduct ultrasound.

Figure 3:
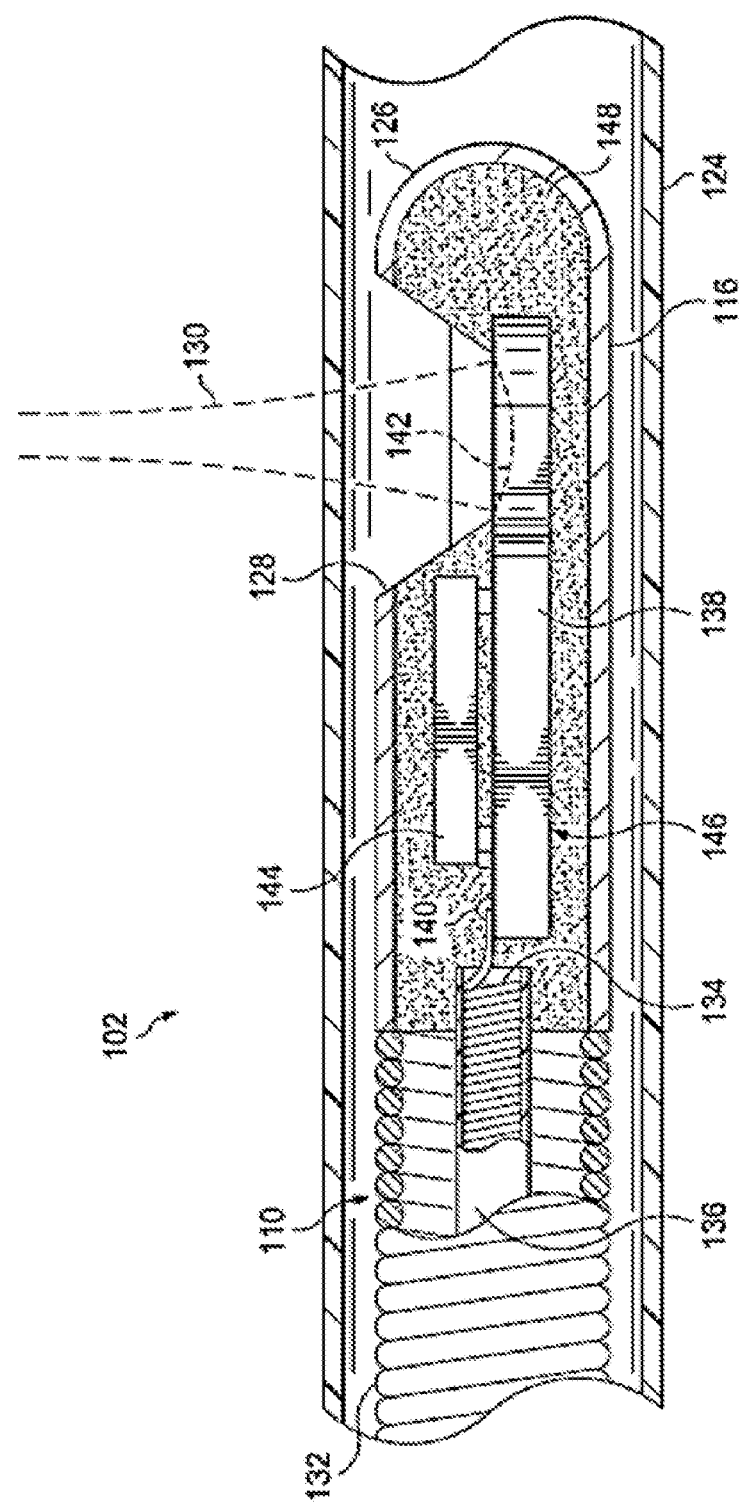
FIG. 3 is a diagrammatic, cross-sectional side view of a distal portion of the imaging device of FIG. 2.

Referring now to FIG. 3, shown therein is a cross-sectional side view of a distal portion of the catheter 102 according to an embodiment of the present disclosure. In particular, FIG. 3 shows an expanded view of aspects of the distal portion of the imaging core 110. In this exemplary embodiment, the imaging core 110 is terminated at its distal tip by a housing 116 fabricated from stainless steel and provided with a rounded nose 126 and a cutout 128 for the ultrasound beam 130 to emerge from the housing 116. In some embodiments, the flexible driveshaft 132 of the imaging core 110 is composed of two or more layers of counter wound stainless steel wires, welded, or otherwise secured to the housing 116 such that rotation of the flexible driveshaft also imparts rotation on the housing 116. In the illustrated embodiment, the PMUT MEMS 138 includes a spherically focused transducer 142 and carries an application-specific integrated circuit (ASIC) 144. The ASIC 144 is electrically coupled to the PMUT MEMS 138 through two or more connections. In that regard, in some embodiments of the present disclosure the ASIC 144 includes an amplifier, a transmitter, and a protection circuit associated with the PMUT MEMS as discussed above. In some embodiments, the ASIC 144 is flip-chip mounted to the substrate of the PMUT MEMS 138 using anisotropic conductive adhesive or suitable alternative chip-to-chip bonding method. When assembled together the PMUT MEMS 138 and the ASIC 144 form an ASIC/MEMS hybrid assembly 146 that is mounted within the housing 116. An electrical cable 134 with optional shield 136 is attached to the ASIC/MEMS hybrid assembly 146 with solder 140. The electrical cable 134 extends through an inner lumen of the flexible driveshaft 132 to the proximal end of the imaging core 110 where it is terminated to the electrical connector portion of the rotational interface 114 shown in FIG. 2. In the illustrated embodiment, the ASIC/MEMS hybrid assembly 146 is secured in place relative to the housing 116 by an epoxy 148 or other bonding agent. The epoxy 148 also serves as an acoustic backing material to absorb acoustic reverberations propagating within the housing 116 and as a strain relief for the electrical cable 134 where it is soldered to the ASIC/MEMS hybrid assembly 146.

Figure 4:
FIG. 4 is a diagrammatic side view of components of the distal portion of the imaging device shown in FIG. 3, including a MEMS component and an ASIC component, according to the present disclosure.
Figure 5:
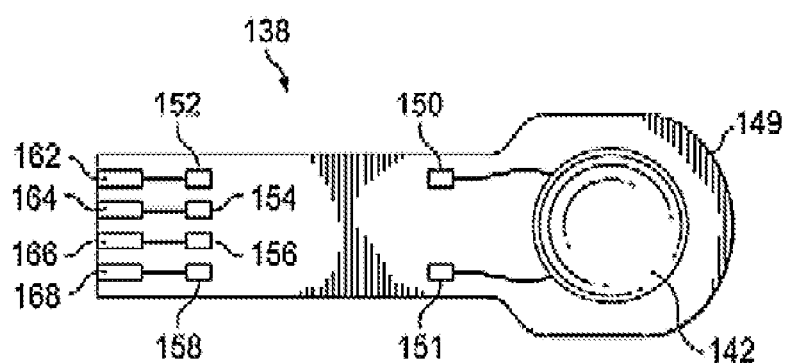
FIG. 5 is a diagrammatic top view of the ASIC component of the components illustrated FIG. 4.

Referring now to FIGS. 4 and 5, shown therein are additional aspects of the PMUT MEMS component 138 and ASIC 144 that form the ASIC/MEMS hybrid assembly 146. The MEMS component 138 in the embodiment of FIGS. 4 and 5 is a paddle-shaped silicon component with the piezoelectric polymer transducer 142 located in the widened portion 149 of the substrate located at the distal end of the MEMS component 138. The narrow portion of the substrate positioned proximal of the widened portion 149 is where the ASIC 144 is mounted to the MEMS component 138. In that regard, the MEMS component 138 includes ten bond pads, with bond pads 150, 151, 152, 154, 156, and 158 of the MEMS 138 configured to match up respectively with six bond pads on the ASIC 144 when the ASIC is flip-chip mounted onto the MEMS 138. The flip-chip mounting is accomplished using anisotropic conductive adhesive, gold-to-gold thermosonic bonding, and/or other suitable method. Solder reflow is not convenient for this application in some instances, since the copolymer transducer element is subject to depoling at temperatures as low as 100° C., well below conventional soldering temperatures. Anisotropic conductive adhesive can be cured at temperatures below 100° C., as long as the cure time is increased to account for the low cure temperature. In this embodiment, the bond pads 152, 154, 156, and 158 are coupled to bond pads 162, 164, 166, and 168 by conductive traces included on the MEMS substrate, with the bond pads 162, 164, 166, and 168 serving as terminations for the four conductors of the electrical cable 134, shown in FIG. 3. In that regard, the transfer of signals over the four conductors can be as described in U.S. Pat. No. 8,864,674 titled "CIRCUIT ARCHITECTURES AND ELECTRICAL INTERFACES FOR ROTATIONAL INTRAVASCULAR ULTRASOUND (IVUS) DEVICES," which is hereby incorporated by reference in its entirety. The four conductors of the electrical cable 134 can be electrically coupled to the MEMS component 138 using one or more of the techniques described below with respect to FIGS. 8-17c. In other embodiments, the four conductors of the electrical cable 134 are soldered or otherwise fixedly attached directly to the ASIC 144. For example, the four conductors of the electrical cable 134 can be electrically coupled to the ASIC 144 using one or more of the techniques described below with respect to FIGS. 8-17c.

Figure 6:
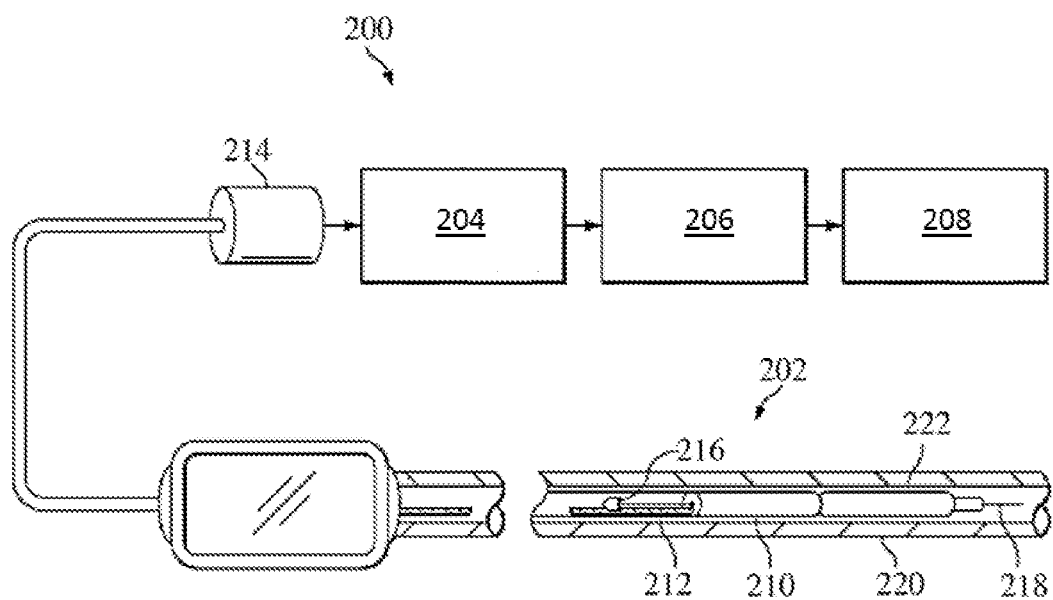
FIG. 6 is a diagrammatic schematic view of an imaging system according to the present disclosure.

Referring now to FIG. 6, shown therein is a diagrammatic schematic view of an intravascular ultrasound (IVUS) imaging system 200 according to an embodiment of the present disclosure. In some embodiments, the IVUS imaging system 200 is a phased-array ultrasound imaging system. In some particular embodiments of the present disclosure, the IVUS imaging system 200 is a piezoelectric zirconate transducer (PZT) solid-state IVUS imaging system. In some embodiments, the system 200 incorporates capacitive micromachined ultrasonic transducers (CMUTs), and/or piezoelectric micromachined ultrasound transducers (PMUTs). The IVUS imaging system 200 may include an IVUS catheter 202, a patient interface module (PIM) 204, an IVUS console or processing system 206, and/or a monitor 208.

At a high level, the IVUS catheter 202 emits ultrasonic energy from a scanner assembly 210 at the tip of the device. The ultrasonic energy is reflected by tissue structures surrounding the scanner 210 and the echo signals from the tissue are received and amplified by the scanner 210.

The PIM 204 facilitates communication of signals between the IVUS console 206 and the IVUS catheter 202 to control the operation of the scanner assembly 210. This includes generating control signals to configure the scanner and trigger the transmitter circuits and transferring echo signals captured by the scanner assembly 210 to the IVUS console 206. With regard to the echo signals, the PIM 204 forwards the received signals and, in some embodiments, performs preliminary signal processing prior to transmitting the signals to the console 206. In examples of such embodiments, the PIM 204 performs amplification, filtering, and/or aggregating of the data. In an embodiment, the PIM 204 also supplies high- and low-voltage DC power to support operation of the circuitry within the scanner 210.

The IVUS console 206 receives the echo data from the scanner 210 by way of the PIM 204 and processes the data to create an image of the tissue surrounding the scanner 210. The console 206 may also display the image on the monitor 208.

In some embodiments, the IVUS catheter includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS catheter 202 includes the ultrasound scanner assembly 210 at a distal end of the device 202 and a cable 212 extending along the longitudinal body of the device 202. The cable 212 terminates in a connector 214 at a proximal end of the device 202. The connector 214 electrically couples the cable 212 to the PIM 204 and physically couples the IVUS catheter 202 to the PIM 204. In an embodiment, the IVUS catheter 202 further includes a guide wire exit port 216. Accordingly, in some instances the IVUS catheter is a rapid-exchange catheter. The guide wire exit port 216 allows a guide wire 218 to be inserted towards the distal end in order to direct the device 202 through a vessel 220. Vessel 220 represents fluid filled or surrounded structures, both natural and man-made, within a living body that may be imaged and can include for example, but without limitation, structures such as: organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to imaging natural structures, the images may also include imaging man-made structures such as, but without limitation, heart valves, stents, shunts, filters and other devices positioned within the body. In an embodiment, the IVUS catheter 202 also includes an inflatable balloon portion 222 near the distal tip. The balloon portion 222 is open to a lumen that travels along the length of the IVUS catheter and ends in an inflation port. The balloon 222 may be selectively inflated and deflated via the inflation port.

The IVUS catheter 202 is designed to provide high-resolution imaging from within narrow passageways. To advance the performance of IVUS imaging devices compared to the current state of the art, embodiments of the present disclosure incorporate advanced transducer technologies, such as PMUT, that offer wide bandwidth (>100%). The broad bandwidth is important for producing a short ultrasound pulse to achieve optimum resolution in the radial direction. The improved resolution provided by PMUT and other advanced ultrasound transducer technologies facilitates better diagnostic accuracy, enhances the ability to discern different tissue types, and enhances the ability to accurately ascertain the borders of the vessel lumen. Embodiments of the present disclosure also have improved flexibility and reduced diameter allowing greater maneuverability and leading to increased patient safety and comfort. Specific embodiments also provide faster, more accurate, and less expensive methods of manufacturing the device 202.

Figure 7:
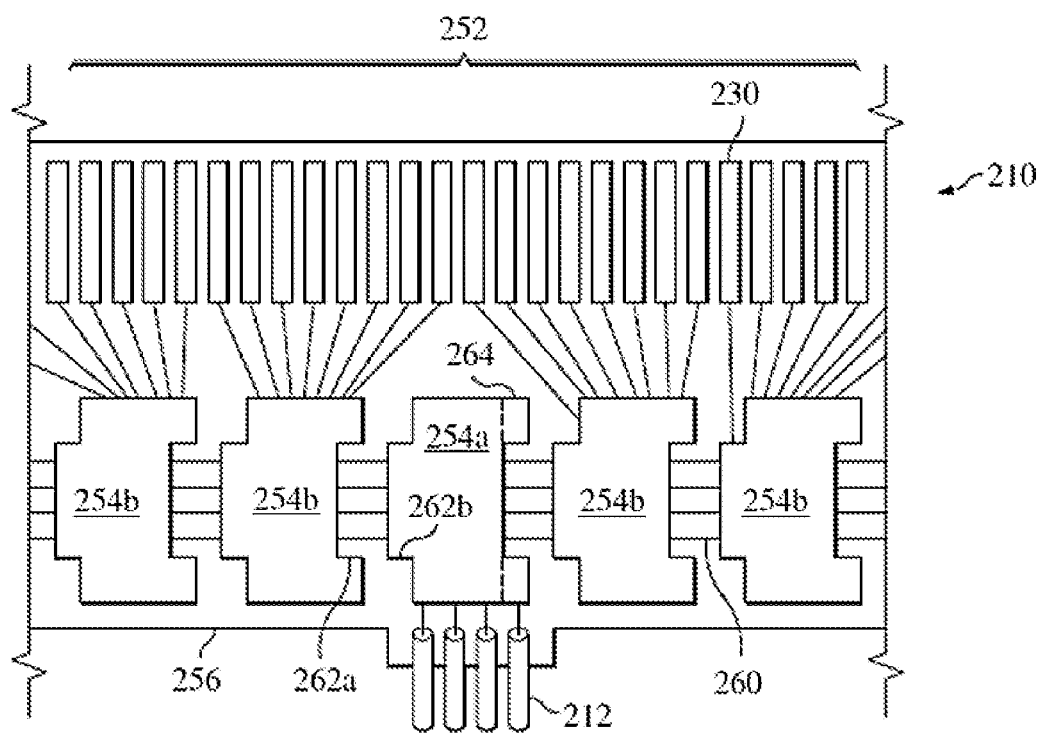
FIG. 7 is a top view of a portion of an ultrasound scanner assembly depicted in its flat form according to the present disclosure.

Referring now to FIG. 7, shown therein is a top view of a portion of an ultrasound scanner assembly 210 according to an embodiment of the present disclosure. FIG. 7 depicts the ultrasound scanner assembly 210 in its flat form. The assembly 210 includes a transducer array 252 and transducer control circuits 254 (including controllers 254a and 254b) attached to a flex circuit 256. As indicated by the common reference numbers, the ultrasound transducers 230 of the transducer array 252 can be substantially similar or identical to one another. The transducer array 252 may include any number and type of ultrasound transducers 230, although for clarity only a limited number of ultrasound transducers are illustrated in FIG. 7. In an embodiment, the transducer array 252 includes 64 individual ultrasound transducers 230. In a further embodiment, the transducer array 252 includes 32 ultrasound transducers. Other numbers are both contemplated and provided for. In an embodiment, the ultrasound transducers 230 of the transducer array 252 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

In the illustrated embodiment, scanner 210 having 64 ultrasound transducers 230 includes nine transducer control circuits 254, of which five are shown. Designs incorporating other numbers of transducer control circuits 254 including 8, 9, 16, 17 and more are utilized in other embodiments. In some embodiments, a single controller is designated a master controller and configured to transfer signals to and from the four conductors of the cable 212. In this regard, the four conductors of the electrical cable 212 can be attached to master controller using one or more of the techniques described below with respect to FIGS. 8-17c. The remaining controllers are slave controllers. In the depicted embodiment, the master controller 254a does not directly control any transducers 230. In other embodiments, the master controller 254a drives the same number of transducers 230 as the slave controllers 254b or drives a reduced set of transducers 230 as compared to the slave controllers 254b. In the illustrated embodiment, a single master controller 254a and four slave controllers 254b are provided. Eight transducers are assigned to each slave controller 254b. Such controllers may be referred to as 8-channel controllers based on the number of transducers they are capable of driving.

The master controller 254a generates control signals for the slave controllers 254b based on configuration data and transmit triggers received via the cable 212. The master controller 254a also receives echo data from slave controllers 254b and retransmits it on the cable 212. To do so, in some embodiments, the master controller 254a includes an echo amplifier. In this configuration, the master controller 254a receives unamplified or partially amplified echo data and performs the necessary amplification for driving the echo data along the conductors of the cable 212. This may provide additional room for a larger high-fidelity amplifier. The transfer of signals over the four conductors of the cable 212, master controller 254a, and slave controllers 254b can be as described in U.S. Patent Application Publication No. 2014/0187960 titled "INTRAVASCULAR ULTRASOUND IMAGING APPARATUS, INTERFACE ARCHITECTURE, AND METHOD OF MANUFACTURING," which is hereby incorporated by reference in its entirety.

In an embodiment, the flex circuit 256 provides structural support and physically connects the transducer control circuits 254 and the transducers 230. The flex circuit 256 may contain a film layer of a flexible polyimide material such as KAPTON™ (trademark of DuPont). Other suitable materials include polyester films, polyimide films, polyethylene napthalate films, or polyetherimide films, other flexible printed circuit substrates as well as products such as Upilex® (registered trademark of Ube Industries) and TEFLON® (registered trademark of E.I. du Pont). The film layer is configured to be wrapped around a ferrule to form a cylindrical toroid in some instances. Therefore, the thickness of the film layer is generally related to the degree of curvature in the final assembled scanner 210. In some embodiments, the film layer is between 5 μm and 100 μm, with some particular embodiments being between 12.7 μm and 25.1 μm.

In an embodiment, the flex circuit 256 further includes conductive traces 260 formed on the film layer. Conductive traces 260 carry signals between the transducer control circuits 254 and the transducers 230 and can provide a set of pads or other structures for connecting the conductors of cable 212. Suitable materials for the conductive traces 260 include copper, gold, aluminum, silver, tantalum, nickel, and tin and may be deposited on the flex circuit 256 by processes such as sputtering, plating, and etching. In an embodiment, the flex circuit 256 includes a chromium adhesion layer. The width and thickness of the conductive traces are selected to provide proper conductivity and resilience when the flex circuit 256 is rolled. In that regard, an exemplary range for the thickness of a conductive trace 260 is between 10-50 μm. For example, in an embodiment, 20 μm conductive traces 260 are separated by 20 μm of space. The width of a conductive trace 260 may be further determined by the size of a pad or other connection structures or the width of a wire to be coupled to the trace.

As the circuit may be rolled to form the finished scanner assembly, the control circuits 254, including both master and slave controllers, may be shaped accordingly. This may include a control circuit 254 edge configured to interface with an edge of an adjacent control circuit 254. In some embodiments, the control circuits 254 include interlocking teeth 262a and 262b. For example, control circuits 254 may be formed with a recess and projection 262a that interlocks with a recess and projection 262b of an adjacent control circuit 254 to form a box joint or finger joint. In some embodiments, a control circuit 254 includes a chamfered edge 264, either alone or in combination with a recess and projection. The chamfered edge 264 may be configured to abut an edge of an adjacent control circuit 254. In some such embodiments, the edge of the adjacent controller is chamfered as well. In some embodiments, each of the controllers 254 interlocks with two adjacent controllers utilizing a similar recess and projection interface. Other combinations, including embodiments utilizing a number of different mechanisms, are contemplated and provided for. For example, in an embodiment, edges of slave control circuits interfacing with a master control circuit have a recess and projection configuration with a chamfered region while edges of slave control circuits interfacing with other slave control circuits have a recess and projection configuration without a chamfered region. Edge configurations that interlock adjacent control circuits 254 may allow for closer control circuit spacing 254 and a reduced diameter in the rolled configuration. Such configurations may also interlock to create a rigid structure and thereby provide additional structural support for the rolled scanner assembly.

Referring now to FIGS. 8-17c shown therein are various assemblies with a four-wire interconnection for use in an intravascular ultrasound imaging device in accordance with the present disclosure. In this regard, the features of one or more of the four-wire interconnects shown and discussed below may be utilized in the context of the rotational and/or phased-array imaging systems described above. In particular, the four-wire interconnects are suitable for connecting to an ultrasound assembly within a distal portion of a catheter in some implementations. In the context of a phased-array IVUS device, the four-wire interconnects can allow a significant amount of additional catheter lumen space compared to the industry standard seven-wire connections. This additional space can be used to include additional device functionalities (actuation, additional delivery lumens, additional sensors, etc.) and/or make the device more robust (increased column strength, pushability, flex, ingress protection, etc.). Reducing the number of wires allows an IVUS catheter to have a better flex radius as it goes through tortuous pathways, and more importantly reduces the risk of broken wire or welds (intermittent image, lost image). Further, reducing the number of wires to four allows for more robust connections to the transducer assembly, while remaining integrated within the catheter body and retaining the overall device profile. For example, the interconnects can utilize various wire/transducer contact geometries, crimping, snap fit, screw press fit, interference fit, and/or combinations thereof to create a robust and mechanically stable connection. Further, some interconnect approaches can reduce the overall duration of the wire bonding process while also simplifying the process. As a result, the number of manufacturing errors can be reduced as a result of the improved designs and manufacturing processes, creating labor costs savings and increasing product yield. Further, patient outcomes can be improved as a result of the minimization of procedure delays from replacing devices suffering from loss and/or intermittent images from damaged interconnects. Referring to FIG. 8, shown therein is a perspective view of an assembly 270 with a four-wire interconnection according to the present disclosure. In particular, the assembly 270 shows the scanner assembly 210 of a phased-array ultrasound catheter coupled to four conductors of a cable 212 extending along the length of the catheter. As shown, the four-wire interconnection provides a significant amount of catheter lumen space that can be used to include additional functionalities (actuation, additional delivery lumens, pull wires, angled lumens for navigation, rapid wire exchange mechanics, additional sensors, coatings, etc.), make the catheter body more robust (increased column strength, pushability, flex, ingress protection, etc.), and/or improve the flex radius of the radius as it goes through tortuous pathways. Further, by having fewer electrical connections, the connections can be larger and more robust while still occupying less space, which further reduces the risk of broken wire or welds (intermittent image, lost image).

Referring now to FIGS. 9a-9c, shown therein is an assembly 300 with a four-wire interconnection according to the present disclosure. In particular, FIG. 9a is a top view of the assembly 300; FIG. 9b is a side view of the assembly 300; and FIG. 9c is a proximal end view of the assembly 300. As shown, the assembly 300 includes a component 302 with electrical contacts 304, 306, 308, and 310. The electrical contacts 304, 306, 308, and 310 can be formed or plated with any suitable conductive material, including without limitation gold, copper, silver, nickel, etc. In this regard, the component 302 is representative of a component of an ultrasound assembly to which conductors 314, 316, 318, and 320 are to be electrically coupled to facilitate operation of the ultrasound assembly. Accordingly, the component 302 may be a MEMS, ASIC, controller (master or slave), and/or other component of the ultrasound assembly, which can be a rotational ultrasound assembly (see, e.g., FIGS. 1-5 above) or a phased-array ultrasound assembly (see, e.g., FIGS. 6-8 above).

Each of the conductors 314, 316, 318, and 320 includes a primary section 314a, 316a, 318a, and 320a and a distal section 314b, 316b, 318b, and 320b. As shown, the primary sections 314a, 316a, 318a, and 320a having a cylindrical profile, while the distal sections 314b, 316b, 318b, and 320b have a flattened profile. In some instances, the flattened profile of the distal sections 314b, 316b, 318b, and 320b is created by physically deforming the cylindrical profile of the conductors 314, 316, 318, and 320 (e.g., using a press). In other instances, the conductors 314, 316, 318, and 320 are initially formed with a flattened profile in at least the distal sections 314b, 316b, 318b, and 320b. In some instances, the primary sections and distal sections have a flattened profile. Unless explicitly stated otherwise, the flattened profile does not require the surface(s) of the distal section to be completely flat or planar, but instead simply requires that a width of the conductor (from one side to the other opposing side) is greater than a height or thickness of the conductor (from a top surface to the opposing bottom surface). It is understood that the flattened profile includes cross-sectional profiles having rectangular, rounded rectangular, oval, elliptical, and/or other shapes.

The flattened profile of the distal sections 314b, 316b, 318b, and 320b provides a larger surface area for bonding to the electrical contacts 304, 306, 308, and 310 of the component 302, which are bond pads in the illustrated embodiment of FIGS. 9a-9c. The distal sections 314b, 316b, 318b, and 320b of the conductors 314, 316, 318, and 320 can be mechanically and electrically coupled to the electrical contacts 304, 306, 308, and 310 by soldering, resistance welding, use of a conductive adhesive, and/or combinations thereof. In some implementations, the connections between the conductors 314, 316, 318, and 320 and the electrical contacts 304, 306, 308, and 310 can be encapsulated in an epoxy, parylene, and/or other suitable protective layer(s).

Figure 10A:
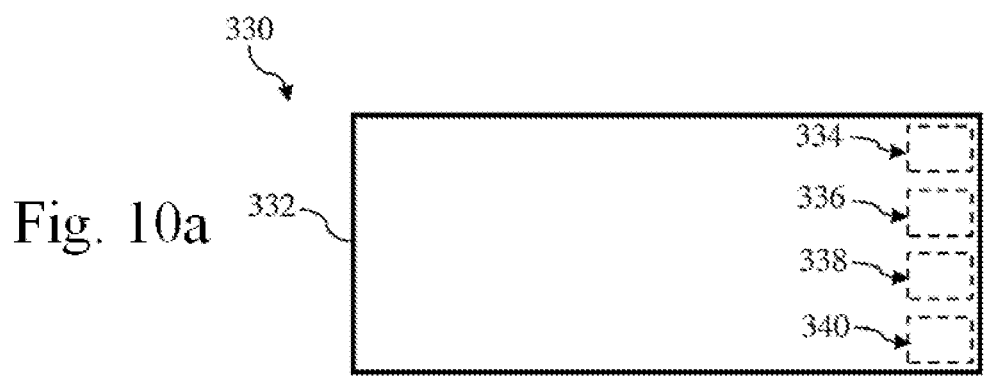
Figure 10B:
FIG. 10b is a side view of the assembly without wires.
Figure 10C:
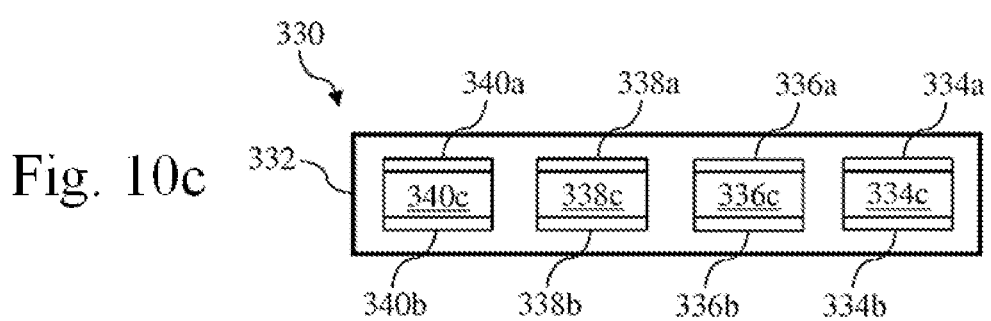
FIG. 10c is a proximal end view of the assembly without wires.
Figure 11A:
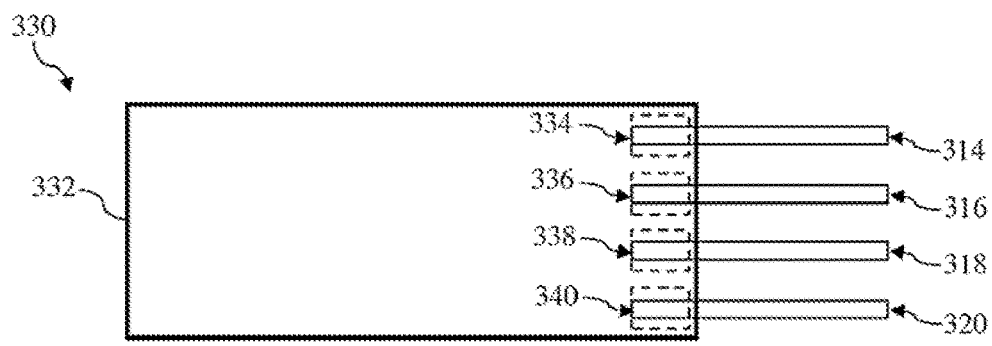
FIG. 11a is a top view of the assembly with wires.
Figure 11B:
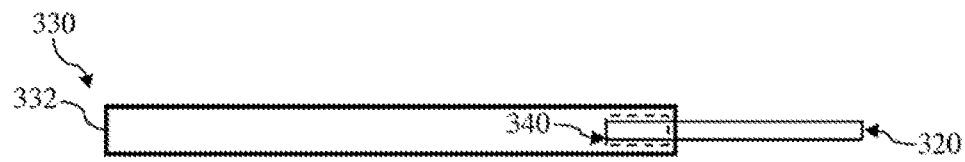
FIG. 11b is a side view of the assembly with wires.
Figure 11C:
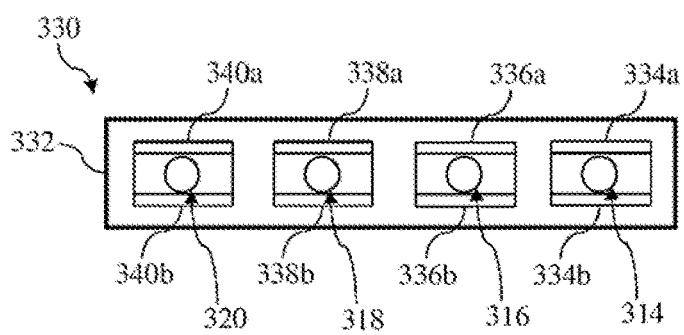

Referring now to FIGS. 10a-11c, shown therein is an assembly 330 with a four-wire interconnection according to the present disclosure. In particular, FIG. 10a is a top view of the assembly 330 without wires; FIG. 10b is a side view of the assembly 330 without wires; FIG. 10c is a proximal end view of the assembly 330 without wires; FIG. 11a is a top view of the assembly 330 with wires 314, 316, 318, and 320 coupled thereto; FIG. 11b is a side view of the assembly 330 with wires 314, 316, 318, and 320 coupled thereto; and FIG. 11c is a proximal end view of the assembly 330 with wires 314, 316, 318, and 320 coupled thereto. As shown, the assembly 330 includes a component 332 with electrical contacts 334, 336, 338, and 340. The electrical contacts 334, 336, 338, and 340 can be formed or plated with any suitable conductive material, including without limitation gold, copper, silver, nickel, etc. In this regard, the component 332 is representative of a component of an ultrasound assembly to which conductors 314, 316, 318, and 320 are to be electrically coupled to facilitate operation of the ultrasound assembly. Accordingly, the component 332 may be a MEMS, ASIC, controller (master or slave), and/or other component of the ultrasound assembly, which can be a rotational ultrasound assembly (see, e.g., FIGS. 1-5 above) or a phased-array ultrasound assembly (see, e.g., FIGS. 6-8 above).

As best seen in FIG. 10c, the electrical contacts 334, 336, 338, and 340 each include an upper portion 334a, 336a, 338a, and 340a and a lower portion 334b, 336b, 338b, and 340b with a space 334c, 336c, 338c, and 340c positioned therebetween, respectively. In this regard, the spaces 334c, 336c, 338c, and 340c between the upper and lower portions of the electrical contacts 334, 336, 338, and 340 are sized and shaped to receive a distal section of the conductors 314, 316, 318, and 320. In some instances, the spaces 334c, 336c, 338c, and 340c between the upper and lower portions of the electrical contacts 334, 336, 338, and 340 are created by forming a sacrificial layer between metal layers and then later removing the sacrificial layer such that the metal layers define the upper and lower portions of the electrical contacts 334, 336, 338, and 340 and the gap left from the removal of the sacrificial layer defines the spaces 334c, 336c, 338c, and 340c.

As best seen in FIG. 11c, the spaces 334c, 336c, 338c, and 340c can be sized to create an interference fit, press fit, and/or loose fit with the distal sections of the conductors 314, 316, 318, and 320. Depending on the mechanical strength of the fit between the distal sections of the conductors 314, 316, 318, and 320 and the upper and lower portions of the electrical contacts 334, 336, 338, and 340, it may be desirable to further secure the conductors to the electrical contacts. To this end, the distal sections of the conductors 314, 316, 318, and 320 can be further coupled to the upper and/or lower portions of the electrical contacts 334, 336, 338, and 340 by soldering, resistance welding, use of a conductive adhesive, use of a non-conductive adhesive, and/or combinations thereof.

Figure 12A:
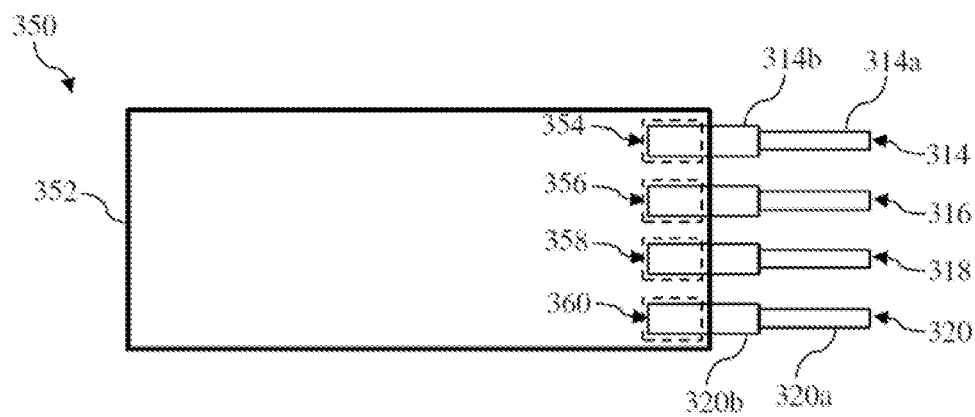
FIGS. 12a-12c illustrate an assembly with a four-wire interconnection according to the present disclosure.
Figure 12B:
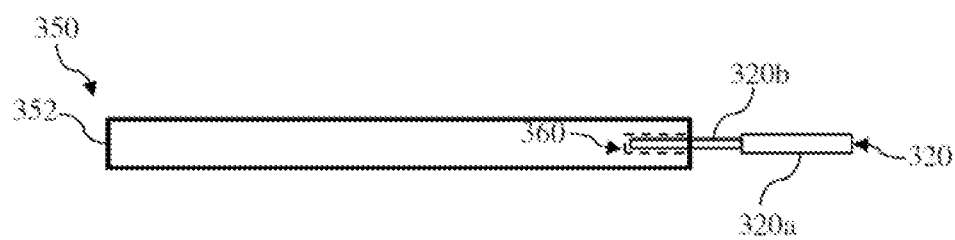
Figure 12C:
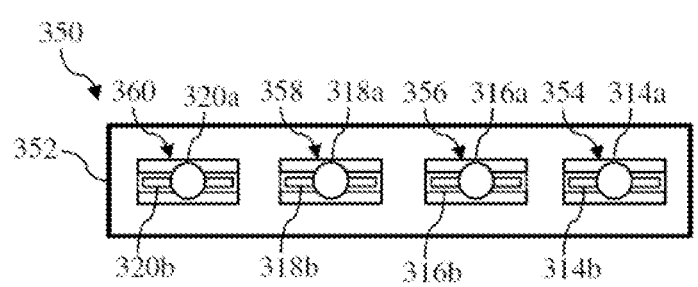

Referring now to FIGS. 12a-12c, shown therein is an assembly 350 with a four-wire interconnection according to the present disclosure. In particular, FIG. 12a is a top view of the assembly 350; FIG. 12b is a side view of the assembly 350; and FIG. 12c is a proximal end view of the assembly 350. As shown, the assembly 350 includes a component 352 with electrical contacts 354, 356, 358, and 360. The electrical contacts 354, 356, 358, and 360 can be formed or plated with any suitable conductive material, including without limitation gold, copper, silver, nickel, etc. In this regard, the component 352 is representative of a component of an ultrasound assembly to which conductors 314, 316, 318, and 320 are to be electrically coupled to facilitate operation of the ultrasound assembly. Accordingly, the component 352 may be a MEMS, ASIC, controller (master or slave), and/or other component of the ultrasound assembly, which can be a rotational ultrasound assembly (see, e.g., FIGS. 1-5 above) or a phased-array ultrasound assembly (see, e.g., FIGS. 6-8 above).

Similar to the assembly 330 described above with respect to FIGS. 10a-11c, the electrical contacts 354, 356, 358, and 360 of the assembly 350 each include an upper portion and a lower portion with a space positioned therebetween. In this regard, the spaces between the upper and lower portions of the electrical contacts 354, 356, 358, and 360 are sized and shaped to receive flattened distal sections 314b, 316b, 318b, and 320b of the conductors 314, 316, 318, and 320. Accordingly, the upper and lower portions of the electrical contacts 354, 356, 358, and 360 are positioned closer to one another in the illustrated embodiment of FIGS. 12a-12c than in the illustrated embodiment of FIGS. 10a-11c. In some instances, the spaces between the upper and lower portions of the electrical contacts 354, 356, 358, and 360 are created by forming a sacrificial layer between metal layers and then later removing the sacrificial layer such that the metal layers define the upper and lower portions of the electrical contacts 354, 356, 358, and 360 and the gap left from the removal of the sacrificial layer defines the spaces therebetween.

In this regard, the spaces between the upper and lower portions of the electrical contacts 354, 356, 358, and 360 can be sized to create an interference fit, press fit, and/or loose fit with the distal sections of the conductors 314, 316, 318, and 320. Depending on the mechanical strength of the fit between the distal sections 314b, 316b, 318b, and 320b of the conductors 314, 316, 318, and 320 and the upper and lower portions of the electrical contacts 354, 356, 358, and 360, it may be desirable to further secure the conductors to the electrical contacts. To this end, the distal sections 314b, 316b, 318b, and 320b of the conductors 314, 316, 318, and 320 can be further coupled to the upper and/or lower portions of the electrical contacts 354, 356, 358, and 360 by soldering, resistance welding, use of a conductive adhesive, use of a non-conductive adhesive, and/or combinations thereof.

Figure 13A:
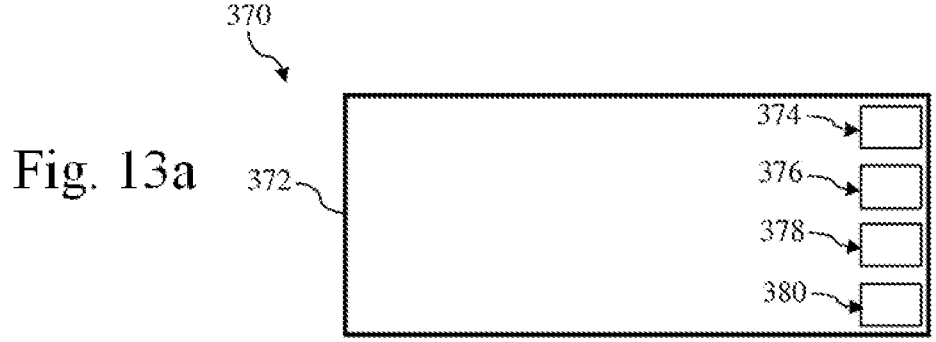
Figure 13B:
FIG. 13b is a side view of the assembly without wires.
Figure 13C:
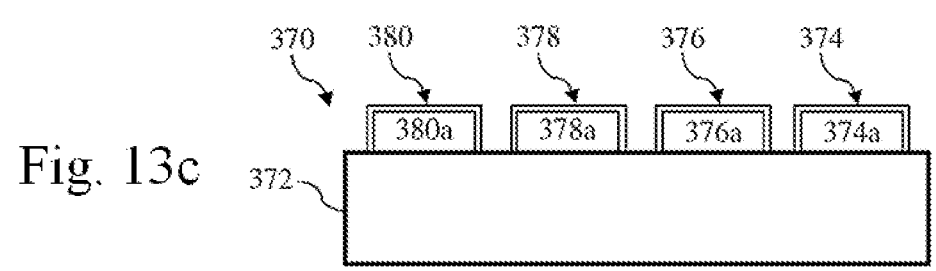
FIG. 13c is a proximal end view of the assembly without wires.
Figure 14A:
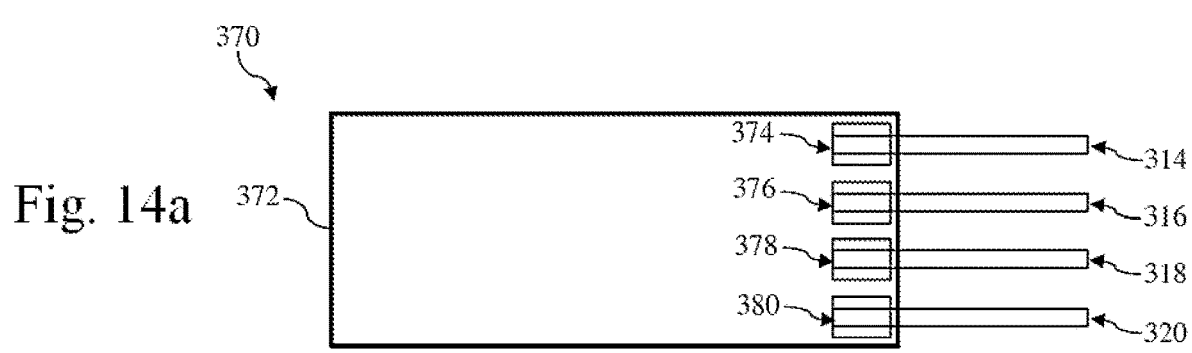
FIG. 14a is a top view of the assembly with wires freely positioned within the assembly.
Figure 14B:
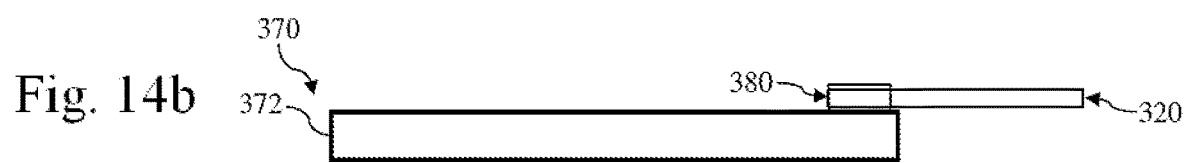
FIG. 14b is a side view of the assembly with wires freely positioned within the assembly.
Figure 14C:
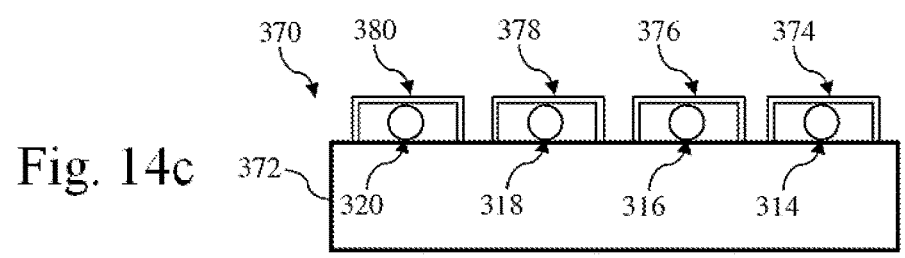
FIG. 14c is a proximal end view of the assembly with wires freely positioned within the assembly.
Figure 15A:
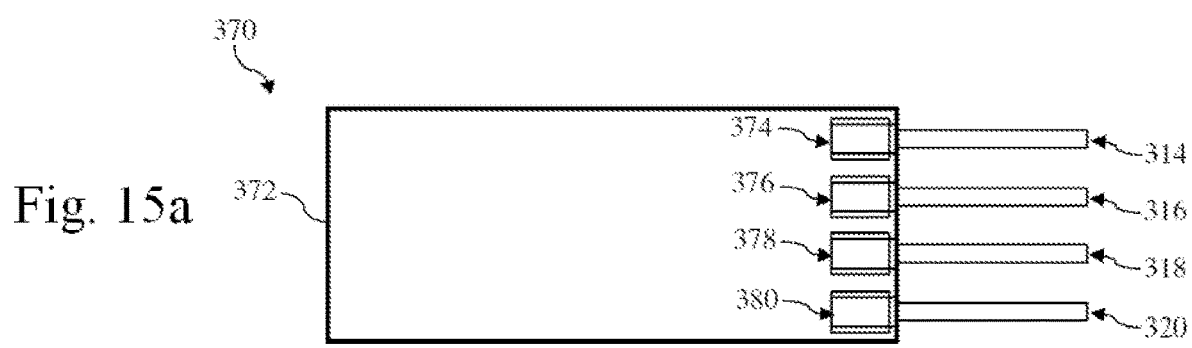
FIG. 15a is a top view of the assembly with wires crimped to the assembly.
Figure 15B:
FIG. 15b is a side view of the assembly with wires crimped to the assembly.
Figure 15C:
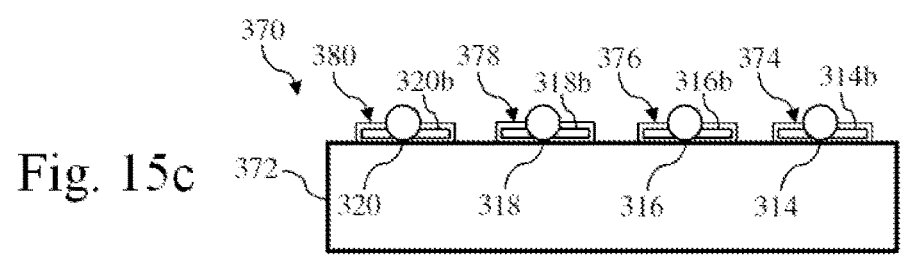

Referring now to FIGS. 13a-15c, shown therein is an assembly 370 with a four-wire interconnection according to the present disclosure. In particular, FIG. 13a is a top view of the assembly 370 without wires; FIG. 13b is a side view of the assembly 370 without wires; FIG. 13c is a proximal end view of the assembly 370 without wires; FIG. 14a is a top view of the assembly 370 with wires 314, 316, 318, and 320 freely positioned within the assembly; FIG. 14b is a side view of the assembly 370 with wires 314, 316, 318, and 320 freely positioned within the assembly; FIG. 14c is a proximal end view of the assembly 370 with wires 314, 316, 318, and 320 freely positioned within the assembly; FIG. 15a is a top view of the assembly 370 with wires 314, 316, 318, and 320 crimped to the assembly; FIG. 15b is a side view of the assembly 370 with wires 314, 316, 318, and 320 crimped to the assembly; and FIG. 15c is a proximal end view of the assembly 370 with wires 314, 316, 318, and 320 crimped to the assembly.

As shown, the assembly 370 includes a component 372 with electrical contacts 374, 376, 378, and 380. The electrical contacts 374, 376, 378, and 380 can be formed or plated with any suitable conductive material, including without limitation gold, copper, silver, nickel, etc. In this regard, the component 372 is representative of a component of an ultrasound assembly to which conductors 314, 316, 318, and 320 are to be electrically coupled to facilitate operation of the ultrasound assembly. Accordingly, the component 372 may be a MEMS, ASIC, controller (master or slave), and/or other component of the ultrasound assembly, which can be a rotational ultrasound assembly (see, e.g., FIGS. 1-5 above) or a phased-array ultrasound assembly (see, e.g., FIGS. 6-8 above).

As best seen in FIG. 13c, the electrical contacts 374, 376, 378, and 380 each define an opening 374a, 376a, 378a, and 380a sized and shaped to receive a distal section of the conductors 314, 316, 318, and 320. In the illustrated embodiment, the conductive material of the electrical contacts 374, 376, 378, and 380 surrounds the openings 374a, 376a, 378a, and 380a on three sides (left, right, and top as seen in FIG. 13c). In other embodiments, the conductive material of the electrical contacts 374, 376, 378, and 380 surrounds the openings 374a, 376a, 378a, and 380a on a greater number of sides (e.g., left, right, top, and bottom) or fewer number of sides (e.g., left and right, top only, etc.).

As best seen in FIG. 14c, the openings 374a, 376a, 378a, and 380a can be sized to initially create an interference fit, press fit, and/or loose fit with the distal sections of the conductors 314, 316, 318, and 320. With the distal sections of the conductors 314, 316, 318, and 320 positioned within the openings 374a, 376a, 378a, and 380a, the electrical contacts 374, 376, 378, and 380 can be crimped onto the distal sections of the conductors 314, 316, 318, and 320 to create an electrical and mechanical coupling therebetween. In this regard, FIGS. 15a-15c illustrate a stylized representation of the electrical contacts 374, 376, 378, and 380 crimped onto the distal sections of the conductors 314, 316, 318, and 320. As shown, the crimping deforms both the electrical contacts 374, 376, 378, and 380 and the distal sections 314b, 316b, 318b, and 320b of the conductors 314, 316, 318, and 320. As a result, the distal sections 314b, 316b, 318b, and 320b of the conductors 314, 316, 318, and 320 have a different profile than the remaining portions of the conductors 314, 316, 318, and 320. In some instances, the crimping causes the distal sections 314b, 316b, 318b, and 320b of the conductors 314, 316, 318, and 320 to take on a flattened profile.

Figure 16A:
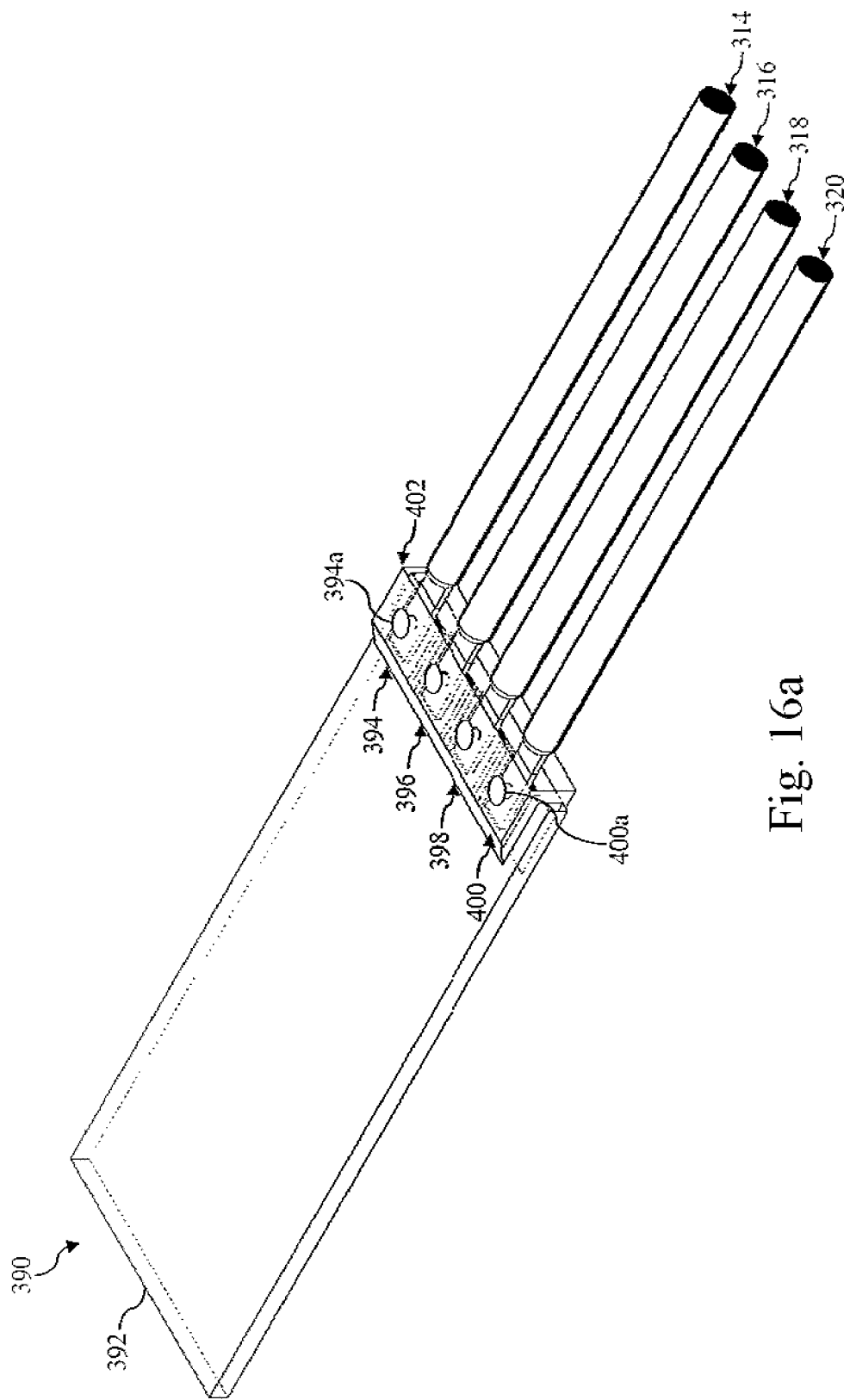
FIGS. 16a-16c illustrate an assembly with a four-wire interconnection according to the present disclosure.
Figure 16B:
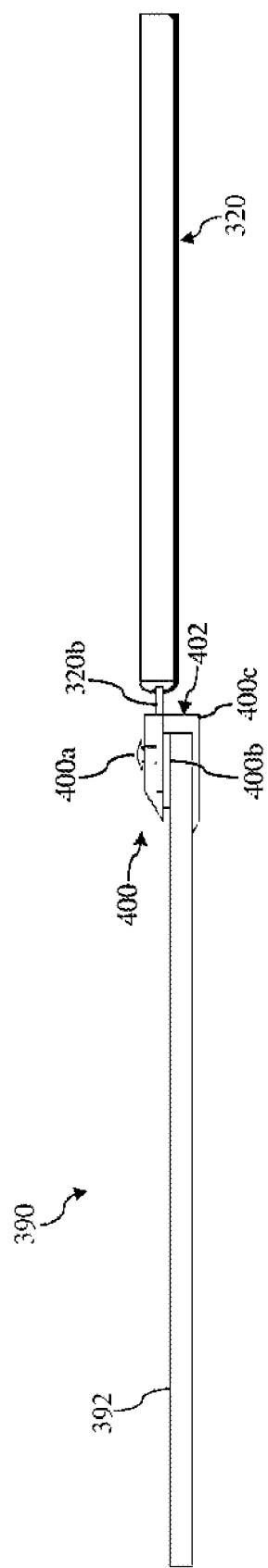
Figure 16C:
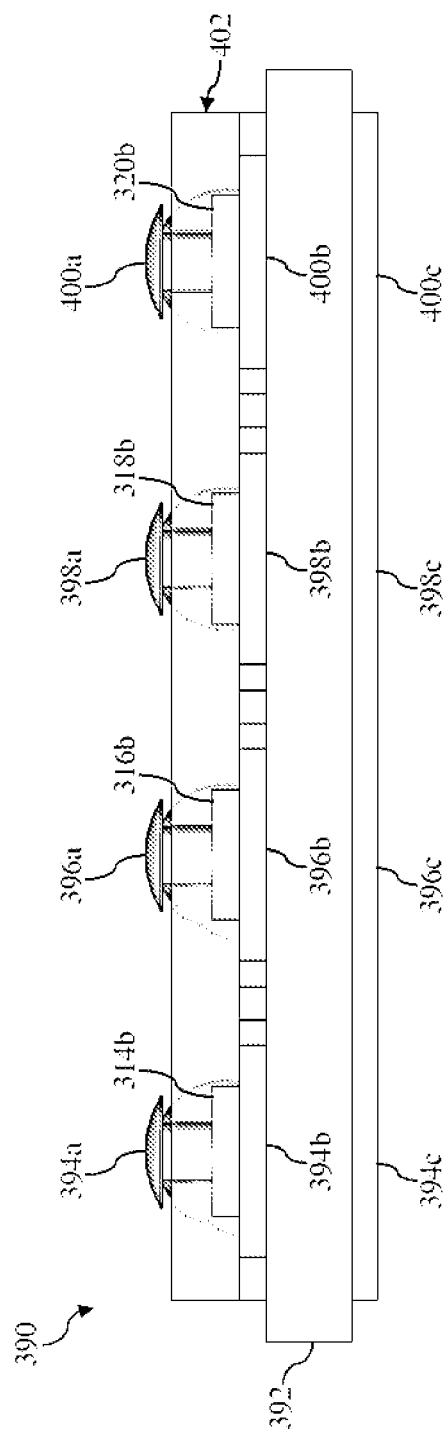

Referring now to FIGS. 16a-16c, shown therein is an assembly 390 with a four-wire interconnection according to the present disclosure. In particular, FIG. 16a is a top view of the assembly 390; FIG. 16b is a side view of the assembly 390; and FIG. 16c is a distal end view of the assembly 390. As shown, the assembly 390 includes a component 392 with electrical contacts 394, 396, 398, and 400. In this regard, the component 392 is representative of a component of an ultrasound assembly to which conductors 314, 316, 318, and 320 are to be electrically coupled to facilitate operation of the ultrasound assembly. Accordingly, the component 392 may be a MEMS, ASIC, controller (master or slave), and/or other component of the ultrasound assembly, which can be a rotational ultrasound assembly (see, e.g., FIGS. 1-5 above) or a phased-array ultrasound assembly (see, e.g., FIGS. 6-8 above).

The electrical contacts 394, 396, 398, and 400 each include a locking component 394a, 396a, 398a, and 400a and an conductive pad 394b, 396b, 398b, and 400b. In this regard, the locking components 394a, 396a, 398a, and 400a are configured to mechanically secure a distal sections 314b, 316b, 318b, and 320b of the conductors 314, 316, 318, and 320 in electrical contact with the conductive pads 394b, 396b, 398b, and 400b. The conductive pads 394b, 396b, 398b, and 400b can be formed or plated with any suitable conductive material, including without limitation gold, copper, silver, nickel, etc. The locking component can be a pin, screw, and/or other component configured to hold the distal sections 314b, 316b, 318b, and 320b of the conductors 314, 316, 318, and 320 in place. In this regard, the locking components 394a, 396a, 398a, and 400a and conductive pads 394b, 396b, 398b, and 400b are coupled with a housing structure configured to receive the distal sections 314b, 316b, 318b, and 320b of the conductors 314, 316, 318, and 320. In the illustrated embodiment, a single housing 402 is provided having corresponding sections 394c, 396c, 398c, and 400c associated with each electrical contact 394, 396, 398, and 400. In other embodiments, separate housings are provided for one or more of the electrical contacts 394, 396, 398, and 400. The housing 402 can be formed during manufacture of the component 392 or attached to the component 392 after manufacture of the component 392. In some instances, the conductive pads 394b, 396b, 398b, and 400b are formed as part of the component 392 and the housing 402 and locking components 394a, 396a, 398a, and 400a are subsequently attached.

Figure 17A:
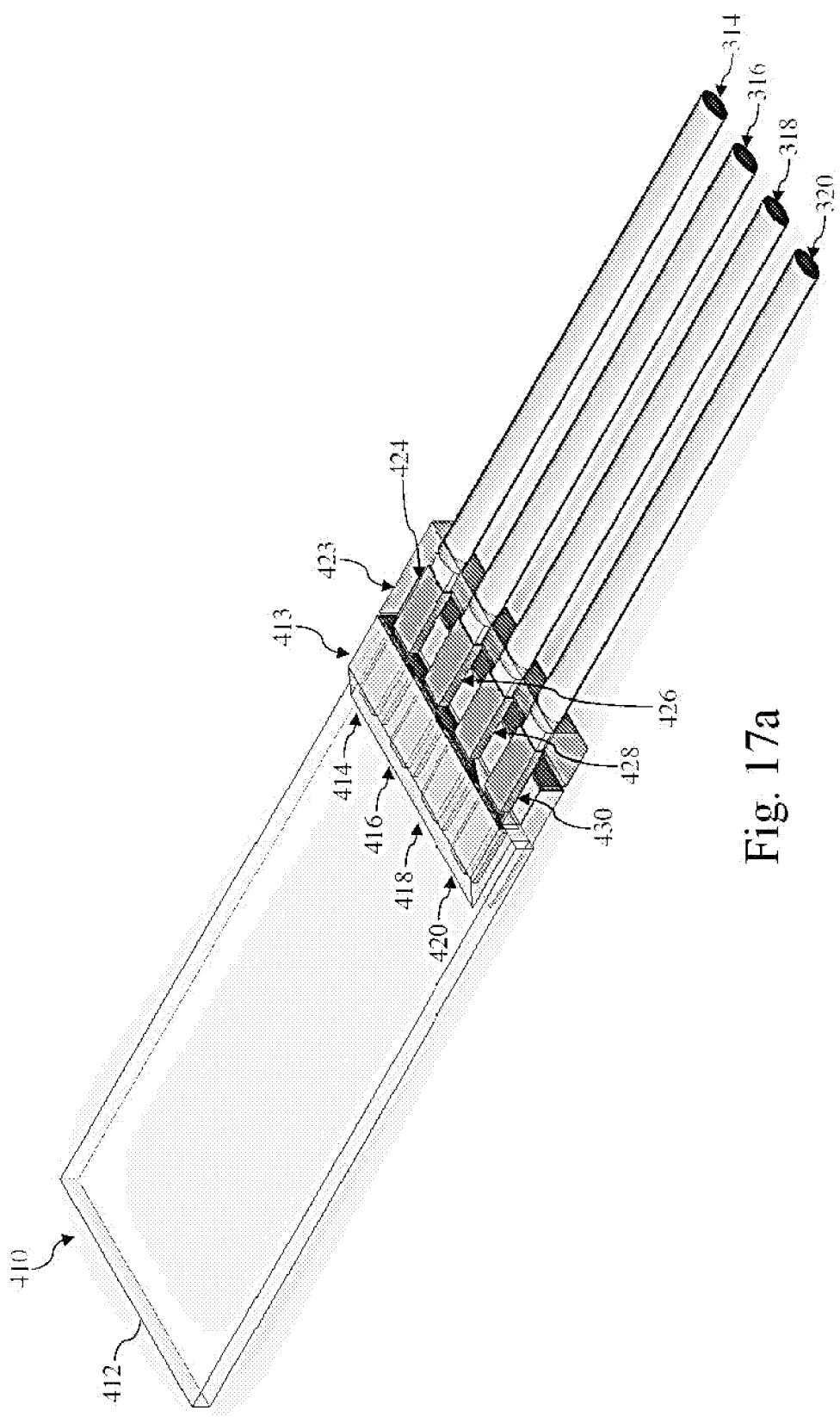
Figure 17B:
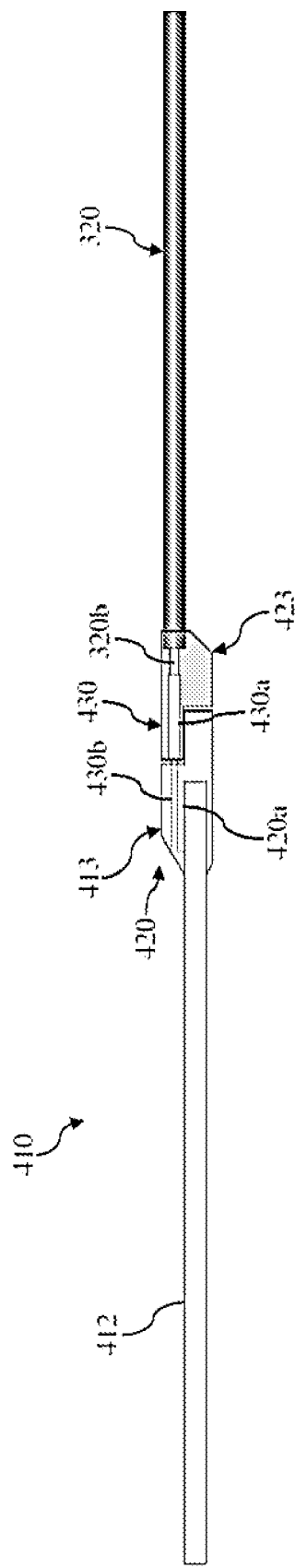

Referring now to FIGS. 17a-17c, shown therein is an assembly 410 with a four-wire interconnection according to the present disclosure. In particular, FIG. 17a is a top view of the assembly 410; FIG. 17b is a side view of the assembly 410; and FIG. 17c is a distal end view of the assembly 410. As shown, the assembly 410 includes a component 412 with a four-contact electrical connector 413 having electrical contacts 414, 416, 418, and 420. In this regard, the component 412 is representative of a component of an ultrasound assembly to which conductors 314, 316, 318, and 320 are to be electrically coupled to facilitate operation of the ultrasound assembly. Accordingly, the component 412 may be a MEMS, ASIC, controller (master or slave), and/or other component of the ultrasound assembly, which can be a rotational ultrasound assembly (see, e.g., FIGS. 1-5 above) or a phased-array ultrasound assembly (see, e.g., FIGS. 6-8 above).

The conductors 314, 316, 318, and 320 are coupled to a four-contact electrical connector 423 having electrical contacts 424, 426, 428, and 430. In this regard, the electrical connectors 413 and 423 are configured to mate with one another such that the electrical contacts 414, 416, 418, and 420 of connector 413 contact the electrical contacts 424, 426, 428, and 430 of connector 423. Accordingly, in some implementations the connector 413 is a female connector and the connector 423 is a male connector. In other implementations the connector 413 is a male connector and the connector 423 is a female connector. In yet other implementations, each connector 413 and 423 is combination male/female connector.

As best seen in FIGS. 17b and 17c, the electrical connector 413 includes conductive pads 414a, 416a, 418a, and 420a. The conductive pads 414a, 416a, 418a, and 420a can be formed or plated with any suitable conductive material, including without limitation gold, copper, silver, nickel, etc. The electrical connector 413 can be formed during manufacture of the component 412 or attached to the component 412 after manufacture of the component 412. In some instances, the conductive pads 414a, 416a, 418a, and 420a are formed as part of the component 412 and the housing defining connector 413 is subsequently attached.

The electrical connector 423 includes electrical connectors 424a, 426a, 428a, and 430a configured to receive distal sections of the conductors 314, 316, 318, and 320, respectively. The electrical connector 423 also includes conductive projections 424b, 426b, 428b, and 430b that are in electrical communication with the electrical connectors 424a, 426a, 428a, and 430a and, therefore, the conductors 314, 316, 318, and 320. The conductive projections 424b, 426b, 428b, and 430b are sized and shaped to interface with the conductive pads 414a, 416a, 418a, and 420a of connector 413 when the connectors 413 and 423 are coupled together. The conductive projections 424a, 426a, 428a, and 430a can be formed or plated with any suitable conductive material, including without limitation gold, copper, silver, nickel, etc.

By having separate electrical connectors 413 and 423, each can be assembled and tested as a sub-component prior to being coupled together. This approach can simplify the manufacturing process, improve yield, and improve the robustness of the electrical connections, which all serve to reduce the number of product malfunctions when the product is subsequently in use. In this regard, it is understood that the connectors illustrated above are exemplary only. It is understood that the connectors can include a single component bridging the conductors to the electrical component(s) of the ultrasound component and/or two or more separate components that mate together. Further, the connectors can utilize interference fits, screw press fits, snap fits, and/or mechanical coupling techniques. Further, the connectors can be manufactured in any suitable manner, including without limitation injection molded, CNC machining, insert molded, etc.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An intravascular ultrasound (IVUS) device, comprising:
   a catheter body;
   an ultrasound assembly coupled to a distal portion of the catheter body; and
   an interconnection with four conductors extending along a length of the catheter body, wherein the four conductors are electrically coupled to electrical contacts of the ultrasound assembly; and
   wherein each of the four conductors includes a primary section and a distal section, wherein the primary sections have a cylindrical profile and the distal sections have a flattened profile.

2. The device of claim 1, wherein the electrical contacts of the ultrasound assembly are bond pads.

3. The device of claim 1, wherein each of the electrical contacts of the ultrasound assembly includes an opening and wherein the distal section of each of the four conductors is positioned within the opening of the respective electrical contact.

4. The device of claim 3, wherein each of the electrical contacts are coupled to an outer surface of the ultrasound assembly, and each of the openings are defined between the respective electrical contact and the outer surface.

5. The device of claim 3, wherein each of the electrical contacts are positioned within the ultrasound assembly, and each of the openings are defined within the ultrasound assembly between two surfaces of the ultrasound assembly.

6. The device of claim 1, wherein the four conductors are electrically coupled to electrical contacts of the ultrasound assembly by at least one of a solder, a resistance weld, a conductive adhesive, a press fit, a crimping, a locking pin and a screw.

7. The device of claim 1, wherein the four conductors are bundled in a cable along at least a portion of the length of the catheter body.

8. The device of claim 1, wherein the ultrasound assembly comprises at least a flexible support element.

9. The device of claim 8, wherein the flexible support element comprises the electrical contacts of the ultrasound assembly.

10. The device of claim 1, wherein each of the electrical contacts of the ultrasound assembly includes a first electrical contact layer separated from a second electrical contact layer by an opening configured to receive a respective distal section of the four conductors, wherein, when positioned within the opening, the respective distal section of each of the four conductors is positioned between and in contact with the first electrical contact layer and the second electrical contact layer of the respective electrical contact.

11. The device of claim 1, wherein the ultrasound assembly is a phased-array ultrasound assembly or a rotational ultrasound assembly.

12. The device of claim 1, wherein the electrical contacts of the ultrasound assembly are in a form of a first four-contact electrical connector, and wherein the four conductors are coupled at their distal ends to a second four-contact electrical connector for electrically and mechanically mating to the first four-contact electrical connector.

13. An intravascular ultrasound (IVUS) system, comprising:
   an IVUS imaging device according to claim 1;
   a proximal connector coupled to a proximal portion of the device, wherein a proximal section of each of the four conductors is coupled to the proximal connector;
   an interface module configured to connect with the proximal connector; and
   an intravascular ultrasound (IVUS) processing component in communication with the interface module.

14. The device of claim 1, wherein each of the electrical contacts of the ultrasound assembly comprises a locking pin configured to mechanically secure a respective conductor of the four conductors to the ultrasound assembly.

15. A method of forming an intravascular imaging device, comprising:
   providing an ultrasound assembly;
   providing an interconnection with four conductors, wherein each of four the conductors includes a primary section and a distal section, wherein the primary sections have a cylindrical profile and the distal sections have a flattened profile;
   electrically coupling a distal section of each of the four conductors to a respective electrical contact of the ultrasound assembly; and
   coupling the ultrasound assembly to a distal portion of a catheter body and extending the four conductors along a length of the catheter body.

16. The method of claim 15, wherein electrically coupling the distal section of each of the four conductors to the respective electrical contact of the ultrasound assembly comprises:
   providing the ultrasound assembly with a first four-contact electrical connector;
   electrically coupling the four conductors to a second four-contact electrical connector; and
   coupling the first and second four-contact electrical connectors together.

17. The method of claim 15, wherein the ultrasound assembly is a phased-array ultrasound assembly or a rotational ultrasound assembly.

* * * * *